(12) United States Patent
Luebke et al.

(10) Patent No.: US 10,626,065 B2
(45) Date of Patent: Apr. 21, 2020

(54) CO-PRODUCTION OF MTBE AND ALKYLATE

(71) Applicant: UOP LLC, Des Plaines, IL (US)

(72) Inventors: Charles P. Luebke, Mount Prospect, IL (US); Christopher D. DiGiulio, Elmhurst, IL (US)

(*) Notice: Subject to any disclaimer, the term of this patent is extended or adjusted under 35 U.S.C. 154(b) by 0 days.

(21) Appl. No.: 16/206,968

(22) Filed: Nov. 30, 2018

(65) Prior Publication Data

US 2019/0185393 A1    Jun. 20, 2019

Related U.S. Application Data

(60) Provisional application No. 62/608,507, filed on Dec. 20, 2017.

(51) Int. Cl.
| | |
|---|---|
| *C07C 5/333* | (2006.01) |
| *C07C 41/06* | (2006.01) |
| *C07C 2/56* | (2006.01) |
| *C07C 5/22* | (2006.01) |
| *C07C 5/02* | (2006.01) |
| *B01J 19/24* | (2006.01) |
| *B01D 3/14* | (2006.01) |
| *B01D 3/00* | (2006.01) |
| *C07C 2/58* | (2006.01) |

(52) U.S. Cl.
CPC ............ *C07C 5/333* (2013.01); *B01D 3/009* (2013.01); *B01D 3/143* (2013.01); *B01J 19/245* (2013.01); *C07C 2/58* (2013.01); *C07C 5/02* (2013.01); *C07C 5/22* (2013.01); *C07C 41/06* (2013.01)

(58) Field of Classification Search
CPC .. C07C 5/333; C07C 5/22; C07C 5/02; C07C 41/06; C07C 2/58; B01J 19/245; B01D 3/143; B01D 3/009
See application file for complete search history.

(56) References Cited

U.S. PATENT DOCUMENTS

| | | | |
|---|---|---|---|
| 3,726,942 A | 4/1973 | Louder | |
| 4,252,541 A | 2/1981 | Herbstman | |
| 4,868,342 A * | 9/1989 | Verson | C07C 9/16 568/697 |
| 2015/0159099 A1 | 6/2015 | Luebke et al. | |
| 2017/0342002 A1 | 11/2017 | Zavala et al. | |

FOREIGN PATENT DOCUMENTS

| | | | |
|---|---|---|---|
| DE | 3718144 A1 * | 12/1987 | ............ C07C 41/06 |
| RU | 2147568 C1 * | 4/2000 | ............... C07C 2/62 |

OTHER PUBLICATIONS

PCT Search Report dated Apr. 4, 2019 for PCT International Application No. PCT/US2018/066635.

* cited by examiner

*Primary Examiner* — Rosalynd A Keys

(57) ABSTRACT

Processes for co-production of methyl tertiary-butyl ether (MTBE) and alkylate is disclosed. The process includes comprising passing a hydrocarbon feed stream comprising $C_4$ hydrocarbons to a dehydrogenation unit to generate a dehydrogenation effluent comprising $C_4$ olefins. The dehydrogenation effluent is passed to a MTBE unit to provide a mixed stream comprising $C_4$ olefins and MTBE. The mixed stream is separated to provide an MTBE product stream and a fractionator overhead stream comprising olefins. The fractionator overhead stream is passed to an alkylation unit to produce an alkylation product stream comprising an alkylate.

15 Claims, 2 Drawing Sheets

CO-PRODUCTION OF MTBE AND ALKYLATE

CROSS-REFERENCE TO RELATED APPLICATION

This application claims priority from U.S. Provisional Application No. 62/608,507 filed Dec. 20, 2017, the contents of which cited application are hereby incorporated by reference in its entirety.

FIELD

The present invention relates to a process for integration of a methyl tertiary-butyl ether (MTBE) unit with alkylation unit for co-production of MTBE and alkylate.

BACKGROUND

A process for the conversion of paraffins to olefins involves passing a normal paraffin stream over a highly selective catalyst, where the normal paraffin is dehydrogenated to the corresponding mono-olefin. The dehydrogenation reaction is achieved under mild operating conditions, thereby minimizing the loss of feedstock.

The typical process involves the use of a radial flow reactor where a paraffin feedstock is contacted with a dehydrogenation catalyst under reaction conditions. For example, the typical linear paraffins in the $C_2$ to $C_{11}$ range may be dehydrogenated to produce olefins which are used as monomers in the formation of polymers, or as plasticizers, or for dehydrogenating paraffins in the $C_{10}$ to $C_{14}$ range to produce linear olefins used in the production of linear alkyl benzenes (LABs), and for dehydrogenating paraffins in the $C_{12}$ to $C_{17}$ range to produce detergent alcohols or olefin sulfonates.

As an example, in sulfuric acid alkylation, it is preferred to employ linear $C_4$ olefins as a feedstock because alkylation with n-butene and isobutane produces higher octane alkylate which leads to high octane gasoline. Typically, olefins are either externally purchased or are obtained from internal refinery streams. Changes in feedstock pricing and feedstock availability may create interest in first producing the linear olefins required, followed by subsequent alkylation.

There is a need to leverage $C_4$ feedstocks to their fullest potential. There is a need for a process and an apparatus for processing $C_4$ feedstocks, which can be tuned to vary the product slate to meet changing product requirements. Other desirable features and characteristics of the present subject matter will become apparent from the subsequent detailed description of the subject matter and the claims, taken in conjunction with the accompanying drawings and this background of the subject matter.

SUMMARY

Various embodiments of a new apparatuses and processes for co-production of tert-butyl ether compound and alkylate have been developed. The process provides co-production of tertiary-butyl ether compound and alkylate through integration of a tertiary-butyl ether unit with alkylation unit.

In accordance with an exemplary embodiment, a process is provided for co-production of tert-butyl ether compound and alkylate comprising passing a hydrocarbon feed stream comprising $C_4$ hydrocarbons to a dehydrogenation unit to generate a dehydrogenation effluent comprising $C_4$ olefins. The dehydrogenation effluent is passed to a tertiary-butyl ether unit to provide a mixed stream comprising $C_4$ olefins and a tertiary-butyl ether compound. The mixed stream is separated to provide a tertiary-butyl ether product stream and a fractionator overhead stream comprising olefins. The fractionator overhead stream is passed to an alkylation unit to produce an alkylation product stream comprising an alkylate.

In accordance with another exemplary embodiment, a process is provided for co-production of methyl tert-butyl ether (MTBE) and alkylate comprising passing a hydrocarbon feed stream comprising $C_4$ hydrocarbons to a dehydrogenation unit to generate a dehydrogenation effluent comprising $C_4$ olefins. The dehydrogenation effluent is passed to a MTBE unit to provide a mixed stream comprising $C_4$ olefins and MTBE. The mixed stream is separated to provide an MTBE product stream and a fractionator overhead stream comprising olefins. The fractionator overhead stream is passed to an alkylation unit to produce an alkylation product stream comprising an alkylate. The alkylation product stream is passed to a de-isobutanizer column to generate a de-isobutanizer overhead stream and a de-isobutanizer bottoms stream. A first portion of the de-isobutanizer overhead stream is passed to the alkylation unit and a second potion of the de-isobutanizer overhead stream is recycled to the dehydrogenation unit. The de-isobutanizer bottoms stream is passed to a debutanizer column to generate a debutanizer overhead stream and the alkylate. A first portion of the debutanizer overhead stream is passed to an isomerization unit to generate an isomerate stream. The isomerate stream is passed to the de-isobutanizer column, wherein an amount of second portion of the de-isobutanizer overhead stream being recycled to the dehydrogenation unit is controlled based on an amount of first portion of the debutanizer overhead stream being passed to the isomerization unit.

In accordance with an exemplary embodiment, an apparatus is provided for co-production of tertiary-butyl ether compound and alkylate comprising a dehydrogenation unit for dehydrogenating a hydrocarbon feed stream comprising $C_4$ hydrocarbons to generate a dehydrogenation effluent comprising $C_4$ olefins. A tertiary-butyl ether unit is in fluid communication with dehydrogenation unit to provide a mixed stream comprising $C_4$ olefins and tertiary-butyl ether compound. A tertiary-butyl ether fractionation column is in fluid communication with the tert-butyl ether unit for separating the mixed stream to provide an tertiary-butyl ether product stream and a fractionator overhead stream comprising olefins in a fractionator overhead line. An alkylation unit is in communication with the tertiary-butyl ether fractionation column to produce an alkylation product stream comprising an alkylate.

These and other features, aspects, and advantages of the present disclosure are further explained by the following detailed description, drawings and appended claims.

BRIEF DESCRIPTION OF THE DRAWINGS

The various embodiments will hereinafter be described in conjunction with the drawings, wherein like numerals denote like elements.

Figure 1:
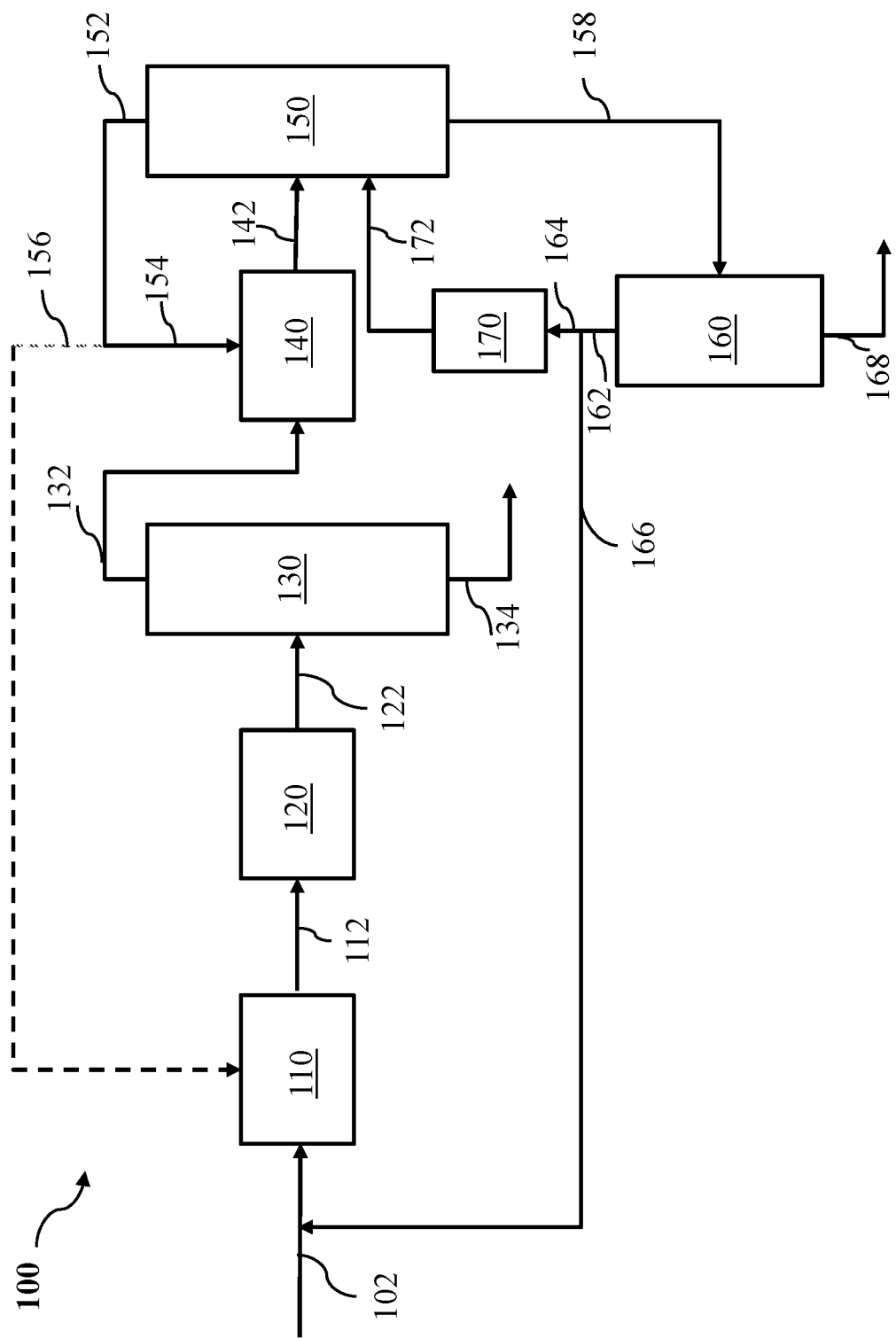
FIG. 1 illustrates the integration of a dehydrogenation unit and an alkylation unit, according to an embodiment of the present disclosure.

Skilled artisans will appreciate that elements in the drawings are illustrated for simplicity and clarity and have not necessarily been drawn to scale. For example, the dimensions of some of the elements in the drawings may be exaggerated relative to other elements to help to improve understanding of various embodiments of the present disclosure. Also, common but well-understood elements that are useful or necessary in a commercially feasible embodiment may not be depicted in order to facilitate a less obstructed view of these various embodiments of the present disclosure.

DETAILED DESCRIPTION

Various embodiments herein relate to processes for co-production of tertiary-butyl ether compound (or tert-butyl ether compound) and alkylate. As used herein, the term "stream" can include various hydrocarbon molecules, such as straight-chain, branched, or cyclic alkanes, alkenes, alkadienes, and alkynes, and optionally other substances, such as gases, e.g., hydrogen, or impurities, such as heavy metals, and sulfur and nitrogen compounds. The stream can also include aromatic and non-aromatic hydrocarbons. Moreover, the hydrocarbon molecules may be abbreviated $C_1$, $C_2$, $C_3$ ... $C_n$ where "n" represents the number of carbon atoms in the one or more hydrocarbon molecules. Furthermore, a superscript "+" or "−" may be used with an abbreviated one or more hydrocarbons notation, e.g., $C_{3+}$ or $C_{3-}$, which is inclusive of the abbreviated one or more hydrocarbons. As an example, the abbreviation "$C_{3+}$" means one or more hydrocarbon molecules of three carbon atoms and/or more.

As used herein, the term "unit" can refer to an area including one or more equipment items and/or one or more zones. Equipment items can include one or more reactors or reactor vessels, heaters, exchangers, pipes, pumps, compressors, and controllers. Additionally, an equipment item, such as a reactor, dryer, or vessel, can further include one or more zones or sub-zones.

The term "column" means a distillation column or columns for separating one or more components of different volatilities. Unless otherwise indicated, each column may include a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Overhead lines and bottom lines refer to the net lines from the column downstream of the reflux or reboil to the column.

As used herein, the term "overhead stream" can mean a stream withdrawn at or near a top of a vessel, such as a column.

As used herein, the term "bottom stream" can mean a stream withdrawn at or near a bottom of a vessel, such as a column.

As used herein, the term "weight percent" may be abbreviated "wt. %" and unless otherwise specified the notation "%" refers to "wt. %"".

As used herein, the term "rich" can mean an amount of at least generally about 50%, and preferably about 70%, by mole, of a compound or class of compounds in a stream.

As depicted, process flow lines in the drawings can be referred to, interchangeably, as, e.g., lines, pipes, branches, distributors, streams, effluents, feeds, products, portions, catalysts, withdrawals, recycles, suctions, discharges, and caustics.

The tertiary-butyl ether compound produced in the instant process can be any suitable tertiary-butyl ether compound, including, but not limited to, methyl tertiary-butyl ether (MTBE) and ethyl tertiary-butyl ether (ETBE). MTBE is the most commonly used tert-butyl ether compound. Consequently, MTBE will be used for ease of discussion. Accordingly, the instant apparatus as described below will be discussed with respect to a MTBE unit.

Arriving now to the FIG. 1, a process and apparatus 100 for co-production of MTBE and alkylate may include a dehydrogenation unit 110, a methyl tertiary-butyl ether (MTBE) unit 120, a MTBE fractionation column 130, an alkylation unit 140, a de-isobutanizer column 150, a debutanizer column 160 and an isomerization unit 170. A hydrocarbon feed stream in line 102 comprising $C_4$ hydrocarbons may be passed to a dehydrogenation unit to generate a dehydrogenation effluent comprising $C_4$ olefins. The hydrocarbon feed stream may include about 10 to about 90 wt. % n-butane and about 10 to about 90 wt. % iso-butane. A second portion of the debutanizer overhead stream in line 166 may be recycled to the dehydrogenation unit 110. A dehydrogenation effluent in line 112 may be withdrawn from the dehydrogenation unit 110. The dehydrogenation effluent may be passed to the MTBE unit 120 to provide a mixed stream in line 122 comprising $C_4$ olefins and MTBE. In accordance with an exemplary embodiment, the dehydrogenation effluent may be passed to a selective hydrogenation unit (not shown) to generate a selective hydrogenation effluent which may be subsequently passed to the MTBE unit.

The mixed stream in line 122 may be passed to MTBE fractionation column 130 for separating the mixed stream to provide a fractionator overhead stream in line 132 comprising olefins and an MTBE product stream in line 134.

The fractionator overhead stream in line 132 may be passed to the alkylation unit 140. The alkyation unit may be a sulfuric acid alkylation unit, an ionic-liquid alkylation unit and the like. An alkylation product stream in line 142 comprising an alkylate is withdrawn from the alkylation unit 140.

Subsequently, the alkylation product stream in line 142 may be passed to a de-isobutanizer column 150 to generate a de-isobutanizer overhead stream in line 152 and a de-isobutanizer bottoms stream in line 158. The de-isobutanizer overhead stream in line 152 may be passed to the alkylation unit 140. In accordance with an exemplary embodiment as shown in FIG. 1, a first portion of the de-isobutanizer overhead stream in line 154 may be passed to the alkylation unit 140. Further, a second potion of the de-isobutanizer overhead stream in line 156 may be passed to the dehydrogenation unit 110. The de-isobutanizer bottoms stream in line 158 may be passed to a debutanizer column 160 to generate a debutanizer overhead stream in line 162 and an alkylate product in line 168. A first portion of the debutanizer overhead stream in line 164 may be passed to an isomerization unit 170. The isomerization unit may be a $C_4$ isomerization unit. The second portion of the debutanizer overhead stream in line 166 may be passed to the dehydrogenation unit 110. In the present disclosure as discussed above, an amount of the second portion of the de-isobutanizer overhead stream 156 being passed to the dehydrogenation unit 110 is controlled based on the amount of the second portion of the debutanizer overhead stream in line 166 being passed to the dehydrogenation unit 110. In an embodiment, the amount of second portion of the de-isobutanizer overhead stream being recycled increases as the amount of second portion of the debutanizer overhead stream being passed to the dehydrogenation unit decreases. In an aspect, the amount of the second portion of the de-isobutanizer overhead stream and the amount of second portion of the debutanizer overhead stream may be controlled using a control system. The amount in line 166 being passed to the dehydrogenation unit 110 may be controlled to vary the amount of MTBE product and the alkylate product and thereby providing flexibility to meet different product slates at different times depending upon the requirement. For example, in an embodiment, when about 100% of overhead stream in line 162 may be routed to the isomerization unit 170 ("Max IsoButane"), excess isobutane so generated may be recycled back to dehydrogenation unit 110 through the line 156 ("Max MTBE"). This mode of operation results in high yield of MTBE product. The control system may include a processor and any suitable structure for interacting with one or more sensors and controlling one or more actuators. The control system could, for example, represent a multivariable controller, such as a Robust Multivariable Predictive Control Technology (RMPCT) controller or other type of controller implementing model predictive control (MPC) or other advanced predictive control (APC). As a particular example, each controller could represent a computing device running a real-time operating system.

In some embodiments, various functions described herein may be implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), Blu-ray or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Referring back to the fractionator overhead stream in line 132, the composition of the fractionator overhead stream is dependent on the composition of the hydrocarbon feed stream with the isobutane to olefin ratio expected to vary from about 0.12 to about 12. For example, when the hydrocarbon feed stream comprises about 90% $nC_4$s, isobutane to olefin ratio is about 0.12. In another example, when the hydrocarbon feed stream comprises about 90% $iC_4$, isobutane to olefin ratio is about 12. In yet another example, when the hydrocarbon feed stream comprises about 40% $iC_4$ and about 60% $nC_4$, the isobutane to olefin ratio may be varied from about 0.5 to 2.6, when operating in max MTBE mode.

An isomerate stream in line 172 is withdrawn from the isomerization unit 170 and may be passed to the de-isobutanizer column 150.

Figure 2:
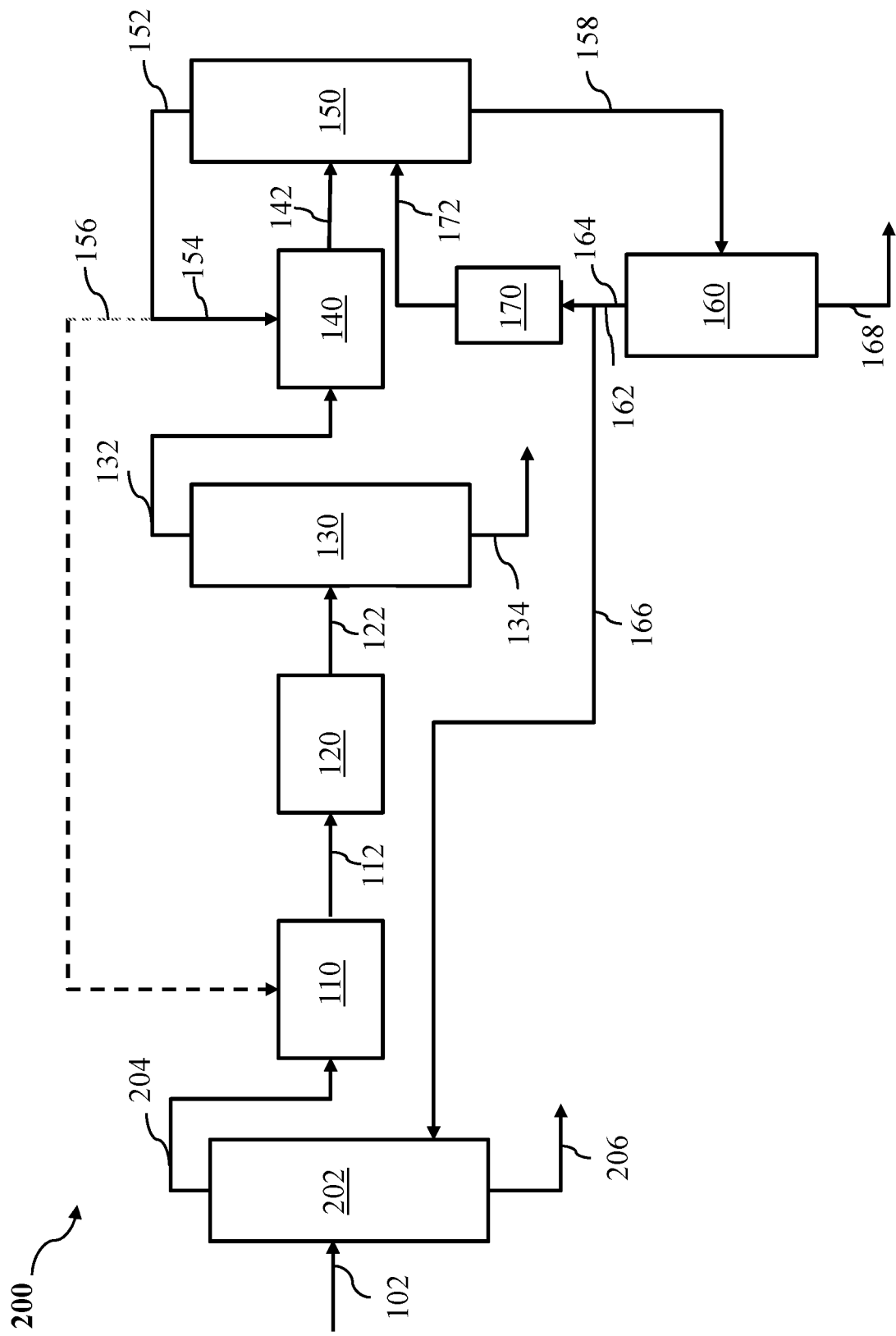
FIG. 2 illustrates the integration of a dehydrogenation unit and an alkylation unit, according to another embodiment of the present disclosure.

Turning now to FIG. 2, another exemplary embodiment of the process and apparatus 200 for isomerizing hydrocarbons is addressed with reference to a process and apparatus 200. Many of the elements in the FIG. 2 have the same configuration as in FIG. 1 and bear the same respective reference number and have similar operating conditions. Elements in FIG. 2 that correspond to elements in FIG. 1 but have a different configuration bear the same reference numeral as in FIG. 1 but are marked with a prime symbol ('). The apparatus and process in FIG. 2 are the same as in FIG. 1 with the exception of the noted following differences. In accordance with the exemplary embodiment as shown in the FIG. 2, the apparatus 200 comprises an additional de-isobutanizer column 202. A hydrocarbon feed stream in line 102' may be passed to the additional de-isobutanizer column 202 to obtain an additional de-isobutanizer overhead stream rich in $C_4$ hydrocarbons which may be subsequently passed to the dehydrogenation unit 110. Further, a second portion of the debutanizer overhead stream in line 166' may also be passed to the additional de-isobutanizer column 202. As shown in the FIG. 2, an additional de-isobutanizer overhead stream rich in butane is withdrawn in line 204, an additional de-isobutanizer bottoms stream comprising $C_{5-}$ hydrocarbons in line 206. Additionally, a side cut stream (not shown) may also be withdrawn from the additional de-isobutanizer column 202. The rest of the process is same as in FIG. 1.

Although not shown, the additional de-isobutanizer column 202 may include a corresponding additional isomerization unit and the side cut stream may be passed to the additional isomerization unit. The additional isomerization unit produces a stream which is sent back to the additional de-isobutanizer.

Applicants have found that the integrated process having a MTBE unit as disclosed in present disclosure allows the user to produce MTBE without adding significant capital expenditure to an integrated dehydrogenation and alkylation process as the MTBE reactors are comparatively inexpensive to dehyrgogenation and alkylation unit. Further, MTBE has even higher octane than alkylate and can be a superior blending stock to achieve high octane blended products. Also, the alkylate product produced has now even higher octane because linear butenes lead to higher octane numbers in sulfuric acid alkylation, as isobutenes are reacted away by the MTBE reactor and more of the linear compounds will pass to the alkylation unit.

Table 1 illustrates the flexibility the instant scheme, as disclosed above, provides in varying the product slate. Case 1 shows the base case without a MTBE unit. Case 2 shows the addition of MTBE unit for a feed comprising about 40 wt. % iso-butane and 60 wt. % n-butane. Case 3 shows how the instant process as disclosed above can shift the amounts of MTBE and alkylate made by adjusting the amount of feed going to isomerization unit. As is shown in the Table 1 below, in case 2 alkylate is the predominant product with some MTBE. However, in case 3, MTBE is the predominant product. In the table below, combined feed refers to the feed comprising the fresh feed and the portion of the debutanizer overhead being recycled to the dehydrogenation unit. Accordingly, the present disclosure as discussed above allows to shift the products without upfront fractionation. Further, the present process provides control to vary the amount of MTBE product and the alkylate product and thereby providing flexibility to meet different product slates at different times depending upon the requirement.

TABLE 1

| Fresh Feed To The Dehydrogenation Unit | Case 1 w/o MTBE | Case 2 w/ MTBE | Case 3 Max MTBE |
|---|---|---|---|
| iC4, mol % | 40 | 40 | 40 |
| nC4, mol % | 60 | 60 | 60 |
| Combined Feed To Dehydrogenation Unit | | | |
| iC4, mol % | 32 | 28 | 67 |
| nC4, mol % | 68 | 72 | 33 |
| Flowrates, kg/hr | | | |

TABLE 1-continued

| Fresh Feed To The Dehydrogenation Unit | Case 1 w/o MTBE | Case 2 w/ MTBE | Case 3 Max MTBE |
|---|---|---|---|
| Fresh Feed | 5812 | 5812 | 5812 |
| Combined Feed to Dehydrogenation Unit | 7266 | 8312 | 10462 |
| MTBE Product | 0 | 1322 | 4143 |
| Alkylate Product | 5712 | 4798 | 2970 |

Specific Embodiments

While the following is described in conjunction with specific embodiments, it will be understood that this description is intended to illustrate and not limit the scope of the preceding description and the appended claims.

A first embodiment of the invention is a process for co-production of a tertiary-butyl ether compound and alkylate, comprising passing a hydrocarbon feed stream comprising $C_4$ hydrocarbons to a dehydrogenation unit to generate a dehydrogenation effluent comprising $C_4$ olefins; passing the dehydrogenation effluent to a tertiary-butyl ether unit to provide a mixed stream comprising $C_4$ olefins and a tertiary-butyl ether compound; separating the mixed stream to provide a tertiary-butyl ether product stream and a fractionator overhead stream comprising olefins; and passing the fractionator overhead stream to an alkylation unit to produce an alkylation product stream comprising an alkylate. An embodiment of the invention is one, any or all of prior embodiments in this paragraph up through the first embodiment in this paragraph, wherein the tertiary-butyl ether compound is one of methyl tertiary-butyl ether (MTBE) or ethyl tertiary-butyl ether (ETBE). An embodiment of the invention is one, any or all of prior embodiments in this paragraph up through the first embodiment in this paragraph further comprising passing the alkylation product stream to a de-isobutanizer column to generate a de-isobutanizer overhead stream and a de-isobutanizer bottoms stream; and passing the de-isobutanizer bottoms stream to a debutanizer column to generate a debutanizer overhead stream and the alkylate. An embodiment of the invention is one, any or all of prior embodiments in this paragraph up through the first embodiment in this paragraph further comprising passing a first portion of the debutanizer overhead stream to an isomerization unit to generate an isomerate stream; and passing the isomerate stream to the de-isobutanizer column. An embodiment of the invention is one, any or all of prior embodiments in this paragraph up through the first embodiment in this paragraph further comprising passing a second portion of the debutanizer overhead stream to the dehydrogenation unit. An embodiment of the invention is one, any or all of prior embodiments in this paragraph up through the first embodiment in this paragraph further comprising passing the hydrocarbon feed stream to an additional de-isobutanizer column to obtain an additional de-isobutanizer overhead stream rich in $C_4$ hydrocarbons and passing the additional de-isobutanizer overhead stream to the dehydrogenation unit. An embodiment of the invention is one, any or all of prior embodiments in this paragraph up through the first embodiment in this paragraph further comprising passing the dehydrogenation effluent to a selective hydrogenation unit to generate a selective hydrogenation effluent and passing the selective hydrogenation effluent to the MTBE reactor. An embodiment of the invention is one, any or all of prior embodiments in this paragraph up through the first embodiment in this paragraph, wherein the alkyation unit is a sulfuric acid alkylation unit. An embodiment of the invention is one, any or all of prior embodiments in this paragraph up through the first embodiment in this paragraph further comprising passing a first portion of the de-isobutanizer overhead stream to the alkylation unit. An embodiment of the invention is one, any or all of prior embodiments in this paragraph up through the first embodiment in this paragraph further comprising recycling a second potion of the de-isobutanizer overhead stream to the dehydrogenation unit. An embodiment of the invention is one, any or all of prior embodiments in this paragraph up through the first embodiment in this paragraph further comprising controlling an amount of the second portion of the de-isobutanizer overhead stream based on the amount of the second portion of the debutanizer overhead stream being passed to the dehydrogenation unit. An embodiment of the invention is one, any or all of prior embodiments in this paragraph up through the first embodiment in this paragraph, wherein the amount of second portion of the de-isobutanizer overhead stream being recycled increases as the amount of second portion of the debutanizer overhead stream being passed to the dehydrogenation unit decreases. An embodiment of the invention is one, any or all of prior embodiments in this paragraph up through the first embodiment in this paragraph, wherein the MTBE fractionation column overhead has an isobutane to olefin ratio varying from about 0.12 to about 12.

A second embodiment of the invention is a process for co-production of methyl tertiary-butyl ether (MTBE) and alkylate, comprising passing a hydrocarbon feed stream comprising $C_4$ hydrocarbons to a dehydrogenation unit to generate a dehydrogenation effluent comprising $C_4$ olefins; passing the dehydrogenation effluent to a MTBE unit to provide a mixed stream comprising $C_4$ olefins and MTBE; separating the mixed stream to provide an MTBE product stream and a fractionator overhead stream comprising olefins; passing the fractionator overhead stream to an alkylation unit to produce an alkylation product stream comprising an alkylate; passing the alkylation product stream to a de-isobutanizer column to generate a de-isobutanizer overhead stream and a de-isobutanizer bottoms stream; passing a first portion of the de-isobutanizer overhead stream to the alkylation unit and recycling a second potion of the de-isobutanizer overhead stream to the dehydrogenation unit; passing the de-isobutanizer bottoms stream to a debutanizer column to generate a debutanizer overhead stream and the alkylate; passing a first portion of the debutanizer overhead stream to an isomerization unit to generate an isomerate stream; and passing the isomerate stream to the de-isobutanizer column; wherein an amount of second portion of the de-isobutanizer overhead stream being recycled to the dehydrogenation unit is controlled based on an amount of first portion of the debutanizer overhead stream being passed to the isomerization unit. An embodiment of the invention is one, any or all of prior embodiments in this paragraph up through the second embodiment in this paragraph further comprising passing a second portion of the debutanizer overhead stream to the dehydrogenation unit, wherein the amount of second portion of the de-isobutanizer overhead stream being recycled increases as the amount of the second portion of the debutanizer overhead stream being passed to the dehydrogenation unit decreases. An embodiment of the invention is one, any or all of prior embodiments in this paragraph up through the second embodiment in this paragraph further comprising passing the hydrocarbon feed stream to an additional de-isobutanizer column to obtain an additional de-isobutanizer overhead stream rich in $C_4$ hydrocarbons and passing the additional de-isobutanizer overhead stream to the dehydrogenation unit. An embodiment of the invention is one, any or all of prior embodiments in this paragraph up through the second embodiment in this paragraph further comprising passing the dehydrogenation effluent to a selective hydrogenation unit to generate a selective hydrogenation effluent and passing the selective hydrogenation effluent to the MTBE reactor. An embodiment of the invention is one, any or all of prior embodiments in this paragraph up through the second embodiment in this paragraph, wherein the alkyation unit is a sulfuric acid alkylation unit.

A third embodiment of the invention is an apparatus for co-production of tertiary-butyl ether compound and alkylate, comprising a dehydrogenation unit for dehydrogenating a hydrocarbon feed stream comprising $C_4$ hydrocarbons to generate a dehydrogenation effluent comprising $C_4$ olefins; a tertiary-butyl ether unit in fluid communication with dehydrogenation effluent line to provide a mixed stream comprising $C_4$ olefins and a tertiary-butyl ether compound; a tertiary-butyl ether fractionation column in fluid communication with the a tertiary-butyl ether unit for separating the mixed stream to provide an a tertiary-butyl ether product stream and a fractionator overhead stream comprising olefins in a fractionator overhead line; and an alkylation unit in fluid communication with the a tertiary-butyl ether fractionation column to produce an alkylation product stream comprising an alkylate. An embodiment of the invention is one, any or all of prior embodiments in this paragraph up through the third embodiment in this paragraph further comprising a de-isobutanizer column in fluid communication with the alkylation unit to generate a de-isobutanizer overhead stream in an de-isobutanizer overhead line and a de-isobutanizer bottoms stream in a de-isobutanizer bottoms line; a debutanizer column in fluid communication with the de-isobutanizer bottoms line to generate a debutanizer overhead stream in a debutanizer overhead line and the alkylate; and an isomerization unit in fluid communication with the debutanizer column to generate an isomerate stream and in communication with the de-isobutanizer column.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for co-production of a tertiary-butyl ether compound and alkylate, comprising:
    passing a hydrocarbon feed stream comprising $C_4$ hydrocarbons to a dehydrogenation unit to generate a dehydrogenation effluent comprising $C_4$ olefins;
    passing the dehydrogenation effluent to a tertiary-butyl ether unit to provide a mixed stream comprising $C_4$ olefins and a tertiary-butyl ether compound;
    separating the mixed stream to provide a tertiary-butyl ether product stream and a fractionator overhead stream comprising olefins;
    passing the fractionator overhead stream to an alkylation unit to produce an alkylation product stream comprising an alkylate;
    passing the alkylation product stream to a de-isobutanizer column to generate a de-isobutanizer overhead stream and a de-isobutanizer bottoms stream;
    passing the de-isobutanizer bottoms stream to a debutanizer column to generate a debutanizer overhead stream and the alkylate;
    passing a first portion of the debutanizer overhead stream to an isomerization to generate an isomerate stream;
    passing the isomerate stream to the de-isobutanizer column; and
    passing a second portion of the debutanizer overhead stream to the dehydrogenation unit.

2. The process of claim 1, wherein the tertiary-butyl ether compound is one of methyl tertiary-butyl ether (MTBE) or ethyl tertiary-butyl ether (ETBE).

3. The process of claim 1 further comprising passing the hydrocarbon feed stream to an additional de-isobutanizer column to obtain an additional de-isobutanizer overhead stream rich in $C_4$ hydrocarbons and passing the additional de-isobutanizer overhead stream to the dehydrogenation unit.

4. The process of claim 1 further comprising passing the dehydrogenation effluent to a selective hydrogenation unit to generate a selective hydrogenation effluent and passing the selective hydrogenation effluent to the MTBE reactor.

5. The process of claim 1, wherein the alkyation unit is a sulfuric acid alkylation unit.

6. The process of claim 1 further comprising passing a first portion of the de-isobutanizer overhead stream to the alkylation unit.

7. The process of claim 1 further comprising recycling a second portion of the de-isobutanizer overhead stream to the dehydrogenation unit.

8. The process of claim 7 further comprising controlling an amount of the second portion of the de-isobutanizer overhead stream based on the amount of the second portion of the debutanizer overhead stream being passed to the dehydrogenation unit.

9. The process of claim 8, wherein the amount of second portion of the de-isobutanizer overhead stream being recycled increases as the amount of second portion of the debutanizer overhead stream being passed to the dehydrogenation unit decreases.

10. The process of claim 1, wherein the MTBE fractionation column overhead has an isobutane to olefin ratio varying from about 0.12 to about 12.

11. A process for co-production of methyl tertiary-butyl ether (MTBE) and alkylate, comprising:
    passing a hydrocarbon feed stream comprising $C_4$ hydrocarbons to a dehydrogenation unit to generate a dehydrogenation effluent comprising $C_4$ olefins;
    passing the dehydrogenation effluent to a MTBE unit to provide a mixed stream comprising $C_4$ olefins and MTBE;
    separating the mixed stream to provide an MTBE product stream and a fractionator overhead stream comprising olefins;
    passing the fractionator overhead stream to an alkylation unit to produce an alkylation product stream comprising an alkylate;
    passing the alkylation product stream to a de-isobutanizer column to generate a de-isobutanizer overhead stream and a de-isobutanizer bottoms stream;

passing a first portion of the de-isobutanizer overhead stream to the alkylation unit and recycling a second portion of the de-isobutanizer overhead stream to the dehydrogenation unit;

passing the de-isobutanizer bottoms stream to a debutanizer column to generate a debutanizer overhead stream and the alkylate;

passing a first portion of the debutanizer overhead stream to an isomerization unit to generate an isomerate stream; and passing the isomerate stream to the de-isobutanizer column;

wherein an amount of second portion of the de-isobutanizer overhead stream being recycled to the dehydrogenation unit is controlled based on an amount of first portion of the debutanizer overhead stream being passed to the dehydrogenation unit.

12. The process of claim 11 further comprising passing a second portion of the debutanizer overhead stream to the dehydrogenation unit, wherein the amount of second portion of the de-isobutanizer overhead stream being recycled increases as the amount of the second portion of the debutanizer overhead stream being passed to the dehydrogenation unit decreases.

13. The process of claim 11 further comprising passing the hydrocarbon feed stream to an additional de-isobutanizer column to obtain an additional de-isobutanizer overhead stream rich in $C_4$ hydrocarbons and passing the additional de-isobutanizer overhead stream to the dehydrogenation unit.

14. The process of claim 11 further comprising passing the dehydrogenation effluent to a selective hydrogenation unit to generate a selective hydrogenation effluent and passing the selective hydrogenation effluent to the MTBE reactor.

15. The process of claim 11, wherein the alkyation unit is a sulfuric acid alkylation unit.

* * * * *